(12) United States Patent
Li et al.

(10) Patent No.: US 12,326,434 B2
(45) Date of Patent: Jun. 10, 2025

(54) METHOD FOR QUANTITATIVELY CHARACTERIZING DENDRITE SEGREGATION AND DENDRITE SPACING OF HIGH-TEMPERATURE ALLOY INGOT

(71) Applicant: NCS TESTING TECHNOLOGY CO., LTD, Beijing (CN)

(72) Inventors: Dongling Li, Beijing (CN); Haizhou Wang, Beijing (CN); Xuejing Shen, Beijing (CN); Lei Zhao, Beijing (CN); Wenyi Cai, Beijing (CN); Mingbo Liu, Beijing (CN); Zongxin Liu, Beijing (CN); Ya Peng, Beijing (CN)

(73) Assignee: NCS TESTING TECHNOLOGY CO., LTD, Beijing (CN)

( * ) Notice: Subject to any disclaimer, the term of this patent is extended or adjusted under 35 U.S.C. 154(b) by 755 days.

(21) Appl. No.: 17/697,938

(22) Filed: Mar. 18, 2022

(65) Prior Publication Data
US 2022/0299455 A1    Sep. 22, 2022

(30) Foreign Application Priority Data

Mar. 19, 2021   (CN) .......................... 202110297432.3

(51) Int. Cl.
*G01N 33/2028*   (2019.01)
*G01N 1/32*   (2006.01)
(Continued)

(52) U.S. Cl.
CPC ........... *G01N 33/2028* (2019.01); *G01N 1/32* (2013.01); *G01N 23/2202* (2013.01); *G01N 23/223* (2013.01); *G01N 2223/076* (2013.01); *G01N 2223/1016* (2013.01); *G01N 2223/3037* (2013.01); *G01N 2223/304* (2013.01);
(Continued)

(58) Field of Classification Search
CPC ..................... G01N 23/2202; G01N 23/223
See application file for complete search history.

(56) References Cited

U.S. PATENT DOCUMENTS

| | | | |
|---|---|---|---|
| 11,927,511 B2 * | 3/2024 | Li | G01N 23/223 |
| 2022/0252488 A1 * | 8/2022 | Li | G01N 1/286 |

FOREIGN PATENT DOCUMENTS

| | | | |
|---|---|---|---|
| CN | 101713751 A | * | 5/2010 |
| CN | 103791862 A | * | 5/2014 |

OTHER PUBLICATIONS

Acer et al., "Effect of Growth Rate on the Microstructure and Microhardness in a Directionally Solidified Al—Zn—Mg Alloy," Metallurgical and Materials Transactions A: 3040—vol. 47A, Jun. 2016. (Year: 2016).*

* cited by examiner

*Primary Examiner* — David P Porta
*Assistant Examiner* — Casey Bryant

(57) ABSTRACT

A method for quantitatively characterizing a dendrite segregation and dendrite spacing of a high-temperature alloy ingot is disclosed. The method includes preparation and surface treatment of the high-temperature alloy ingot, selection of calibration sample and determination of an element content, establishment of quantitative method for elements in micro-beam X-ray fluorescence spectrometer, quantitative distribution analysis of element components of the high-temperature alloy, quantitative characterization of characteristic element line distribution of high-temperature alloy, and analysis of a characteristic element line distribution map and statistics of a secondary dendrite spacing.

9 Claims, 11 Drawing Sheets

(51) Int. Cl.
*G01N 23/2202* (2018.01)
*G01N 23/223* (2006.01)
(52) U.S. Cl.
CPC .................. *G01N 2223/323* (2013.01); *G01N 2223/3307* (2013.01); *G01N 2223/402* (2013.01); *G01N 2223/602* (2013.01); *G01N 2223/63* (2013.01)

METHOD FOR QUANTITATIVELY CHARACTERIZING DENDRITE SEGREGATION AND DENDRITE SPACING OF HIGH-TEMPERATURE ALLOY INGOT

CROSS-REFERENCE TO RELATED APPLICATION

This patent application claims the benefit and priority of Chinese Patent Application No. 2021102974323 filed on Mar. 19, 2021, the disclosure of which is incorporated by reference herein in its entirety as part of the present application.

TECHNICAL FIELD

The present disclosure relates to the technical field of metal material composition and microstructure analysis, in particular to a method for quantitatively characterizing a dendrite segregation and dendrite spacing of a high-temperature alloy ingot.

BACKGROUND ART

Dendrite is a kind of crystal formed by dendritic branching structure in the process of metal solidification. According to the order of dendrite growth, it can be divided into primary dendrites and secondary dendrites. In the solidification process of the liquid metal, the dendrites which grow first along the heat transfer direction and are mutually parallel or show a certain orientation distribution are primary dendrites, and secondary dendrites are the next order dendrites which grow on the arms of primary dendrites and are perpendicular to their growth direction. These dendritic microstructures are the characteristic microstructures produced in the solidification process of metallic materials, and are mainly caused by the element segregation at the solid-liquid interface during the nonequilibrium solidification of alloys. In the condition of rapid cooling, when the liquid alloy crystallize in a dendritic mode, due to the slow diffusion process of atoms in the solid phase, there is a gap between the first precipitated dendrites and the later precipitated dendrites, and finally the dendrite with heterogeneous chemical composition is obtained. The degree of dendrite segregation is determined by the factors such as the cooling rate of the alloy and the diffusion ability of the segregation elements, due to the existence of dendrite segregation, the chemical composition inside the grains and the structure of the ingot are extremely uneven, and the properties of the ingot are seriously deteriorated, therefore, the dendrite segregation must be reduced by improving the technology, and the important characteristic parameter of the dendrite segregation is the segregation ratio of the element, which is obtained by the ratio of the element between dendrites and the dry content of dendrites. The numerical value can reflect the degree of dendrite segregation. The dendrite spacing is also a characteristic parameter characterizing the dendrite structure, the dendrite axis spacing is a function of the solidification conditions, and the local solidification time has an important effect, which is inversely proportional to the average cooling rate, and this parameter has a decisive influence on the properties of the material, and directly affects the thermomechanical properties and heat treatment process of the alloy. Therefore, the quantitative characterization of dendritic segregation and dendritic spacing in ingots is of great significance for analyzing the dynamic equilibrium process of melting-solidification of materials, examining the relationship between melting time (melting rate) and solidification structure, and exploring the rules of element segregation.

High-temperature alloys have the characteristics of many alloying elements and high content, so during solidification, solute redistribution leads to obvious dendritic segregation of alloying elements. therefore, the distribution of elements is closely related to the distribution of dendritic structure. More elements such as Ni, Cr and Fe are enriched in the primary and secondary dendrites, and more elements such as Nb, Mo and Ti are enriched in the dendrites. The width of the dendritic arms of high-temperature alloy is usually 30-100 μm, and the distance between adjacent secondary dendritic arms is usually between 50-100 μm, thus the characterization of the composition distribution is required to have good spatial resolution, at present, the commonly used methods for the characterization of microstructure components are the combination of scanning electron microscopy and energy spectrum analysis, and the electron probe method has a limited field of view for observation, and the quantitative accuracy needs to be improved. Therefore, the calculation of the segregation ratio is subject to a large error. At present, the primary dendrite spacing of high-temperature alloy castings is measured mainly according to the national standard GB/T14999.7-2010, and the tested section used for the primary dendrite spacing measurement is prepared by grinding, polishing and corrosion, then the dendrite structure image is collected by metalloscope, and the average distance of dendrite in a single field of view is obtained by taking the center of each dendrite section as the counting point. The secondary dendrite spacing is usually determined by the method of "quantitative analysis of image" using single primary dendrite with uniform growth of secondary dendrite as the measuring point. These methods have the problems of low efficiency, and the degree of corrosion is difficult to control, and the non-uniformity of corrosion in the large-scale section is easy to exist, which results in the incomplete or unmanifested corrosion of some dendrites. In addition, the single field of view of metallography is limited, but the single field of view or local multiple fields of view can not reflect the distribution characteristics of the whole microstructure of the material. Therefore, in general, the traditional characterization methods for the composition distribution and average spacing of dendritic structures have the problems of small amount of information and insufficient quantitative accuracy, which cannot meet the needs of material workers to investigate the solidification process and improve the material properties.

Therefore, it is necessary to invent a method for quantitatively characterizing dendrite segregation and dendrite spacing of a high-temperature alloy ingot to solve that problem.

SUMMARY

The disclosure aims to provide a method for quantitatively characterizing dendrite segregation and dendrite spacing of a high-temperature alloy ingot, by determining the distribution orientation of the primary dendrite arm and the adjacent primary dendrite spacing according to the solidification segregation characteristic of the high-temperature alloy element and the content two-dimensional distribution diagram of the characteristic element, and calculating the average spacing and segregation ratio of the secondary dendrite arm through the content line distribution diagram of the characteristic element, the sample preparation is simple, and chemical corrosion on the surface of a sample is not required, thereby solving the defects in the technology.

In order to achieve the purpose, the disclosure provides the follow technical scheme: a method for quantitatively characterizing dendrite segregation and dendrite spacing of a high-temperature alloy ingot, wherein the specific operation steps are as follows:

step 1: preparation and surface treatment of the high-temperature alloy ingot, cutting off a certain size block high-temperature alloy ingot sample, and grinding or polishing a characteristic section;

step 2: selection of a calibration sample and determination of an element content, selecting a series of block spectrum standard samples or uniform block alloys with a element composition and structure close to those of the high-temperature alloy sample, measuring a content of each element in the calibration sample by using a national standard method to obtain a chemical composition analysis result of the calibration sample, and grinding or polishing a surface of the calibration sample;

step 3: establishment of a quantitative method for elements in a micro-beam X-ray fluorescence spectrometer, measuring a calibration sample by using the micro-beam X-ray fluorescence spectrometry, obtaining an instrument initial element quantitative analysis result, and performing a linear regression fitting on a chemical component analysis result of step 2 and a fluorescence spectrum initial measurement result to obtain a high-temperature alloy element content calibration equation;

step 4: quantitative distribution analysis of element components of the high-temperature alloy, performing an analysis and test on the high-temperature alloy bulk sample by using the micro-beam X-ray fluorescence spectrometry under the same conditions in step 3, calibrating an element content of the obtained data matrix by using the quantitative calibration equation in step 3 to obtain a two-dimensional distribution map of the content of each element, the distribution orientation of the primary dendritic structure and the space between adjacent primary dendrites;

step 5: quantitative characterization of characteristic element line distribution of high-temperature alloy, according to the two-dimensional element content distribution map obtained in step 4, selecting elements with obvious dendrite distribution characteristics for line distribution quantitative characterization to obtain a characteristic element content line distribution map;

step 6: analysis of a characteristic element line distribution map and statistics of a secondary dendrite spacing, calculating an average spacing of the secondary dendrite and a segregation ratio of the element within the range according to the line distribution map of the characteristic element.

Preferably, in step 1, the size of a section to be measured of the massive polycrystalline high-temperature alloy is larger than 10 mm×10 mm, and the section to be measured is cut along a solidification heat transfer direction of liquid metal.

Preferably, in step 2, the series of bulk spectral standard samples or uniform bulk alloy matrix are matched with the sample to be tested, all elements of the sample to be tested are contained in the series of bulk samples, and the element content of the sample to be tested is also within the range of the maximum value and minimum element content of the series of bulk samples.

Preferably, in step 3, the micro-beam X-ray fluorescence spectrum is provided with a sample moving platform with the repeated positioning accuracy being less than or equal to 3 μm, an analysis beam spot of the micro-beam X-ray fluorescence spectrum is adjustable to 5 μm at least, an instrument initial element quantitative analysis result is a result obtained by a general quantitative method provided by the instrument, and a data result is affected by the composition and structure of a sample and there is a certain deviation between the data and the true content, and a linear regression fitting is performed on the chemical composition analysis result in the step 2 and the fluorescence spectrum initial determination result by a single linear fitting method, and the fitting equation is as follows:

$$C=KC_0+a$$

wherein C0 is the initial element quantitative analysis content of the instrument, C is the content after element calibration, K and a are constants.

Preferably, in step 4, the distribution orientation of the primary dendrite structure is the directionality of the primary dendrite arm of the ingot casting, an included angle mark between the primary dendrite arm and the X direction can be used to form a line segment perpendicular to two adjacent parallel primary dendrite arms, the coordinates of the intersection points with the centers of the two adjacent primary dendrite arms are recorded, and the distance between the adjacent primary dendrites is calculated according to the two point coordinates, and the calculation formula is as follows:

$$D=\sqrt{(X_2-X_1)^2+(Y_2-Y_1)^2}$$

wherein (X1, Y1) is an intersection of a vertical line and the center of the first primary dendritic arm, (X2, Y2) is an intersection of the vertical line and the center of the second primary dendritic arm, and D is an adjacent primary dendritic spacing.

Preferably, in step 5, the high-temperature alloy test rod has elements with obvious characteristic distribution on a dendritic structure, including elements of Nb, Fe, Cr and Ni, and the content of the elements is more than 1%.

Preferably, in step 5, the angle of a line scanning direction is adjusted according to the element intensity or content surface distribution map obtained in the step 4, so that a primary dendritic arm is parallel to the x direction, and the line scanning direction is along the X direction when the secondary dendritic spacing is measured, more than three secondary dendritic arms must be included, the pixel spacing is less than or equal to 5 μm, and a single pixel acquisition time needs to ensure that an element fluorescence signal is more than 10000 cps to ensure the spatial resolution and quantitative reliability of the line distribution.

Preferably, in step 6, the following formula is used to calculate the secondary average spacing:

$$\lambda=(X_2-X_1)/d$$

wherein, X2 is the position when the element content of the secondary dendritic gap on the right side of the line distribution chart has a regional extreme value, X1 is the position when the element content of the secondary dendritic gap on the left side of the line distribution chart has a regional extreme value, D is the number of secondary dendritic arms contained between two locations in the profile.

Preferably, an element segregation ratio (SR) on the secondary dendritic gap and the dendritic arm can be calculated according to the content on the line distribution map, and the calculation formula is:

$$S_R = C_1/C_2$$

wherein C1 is the content of elements on the secondary dendrite gap, and C2 is the content of elements on the secondary dendrite arm.

In the technical scheme, the technical effects and advantages provided by the disclosure are as follows:

1. The disclosure is based on solidification segregation characteristic of the high-temperature alloy element, the distribution orientation of the primary dendritic arm and the adjacent primary dendritic spacing are determined according to the content two-dimensional distribution diagram of the characteristic element, the average spacing and segregation ratio of the secondary dendritic arm are calculated through the content line distribution diagram of the characteristic element, and compared with the traditional micro-zone analysis method and the metallographic method, the sample preparation is simpler, and chemical corrosion on the surface of a sample is not required, through an instrument test method, the quantitative distribution information of components, the segregation ratio data and the dendrite space information in a large range can be obtain, the detection efficiency is greatly improved, the field of view of statistics is large and the information is complete, Statistical data are more accurate and reliable;
2. In the present disclosure, the high-brightness X-ray obtained by the multi-guide capillary focusing technology is excited on the surface of the sample by adopting the micro-beam X-ray fluorescence spectrum technology, the surface depth of the action material is much deeper than that of a scanning electron microscope and an electron probe, the requirement on the surface roughness is not high, and the conductivity of a sample is not strictly required at the same time, the method is suitable for sample analysis of various form, metallographic sample preparation is not required on the surface to be measured, the surface with the roughness meeting the requirement is ground by a grinding machine, and the surface distribution analysis of a sample in a large area and the accurate positioning of a micro area can be realize by matching a high-precision sample platform and a micro-amplifying device;
3. In the present disclosure, the linear regression calibration equation of the element content is obtained by adopting a series of calibration samples with type matching, the element content on the dendritic structure is quantitatively calibrated, and the reliability of component distribution quantification and segregation ratio calculation is ensured; and meanwhile, the elements which can be calibrated by the linear regression calibration equation and the coverage range thereof have better universality than single standard sample calibration.

BRIEF DESCRIPTION OF THE DRAWINGS

Next, the technical solutions in the embodiments of the present disclosure will be clearly and completely described with reference to the drawings in the embodiments of the present disclosure, obviously, the described embodiments are only part of the embodiments of the present disclosure, not all of them. Based on the embodiments in the present disclosure, all other embodiments obtained by ordinary technicians in the field without creative work are within the scope of the present disclosure.

DETAILED DESCRIPTION OF THE EMBODIMENTS

Figure 1:
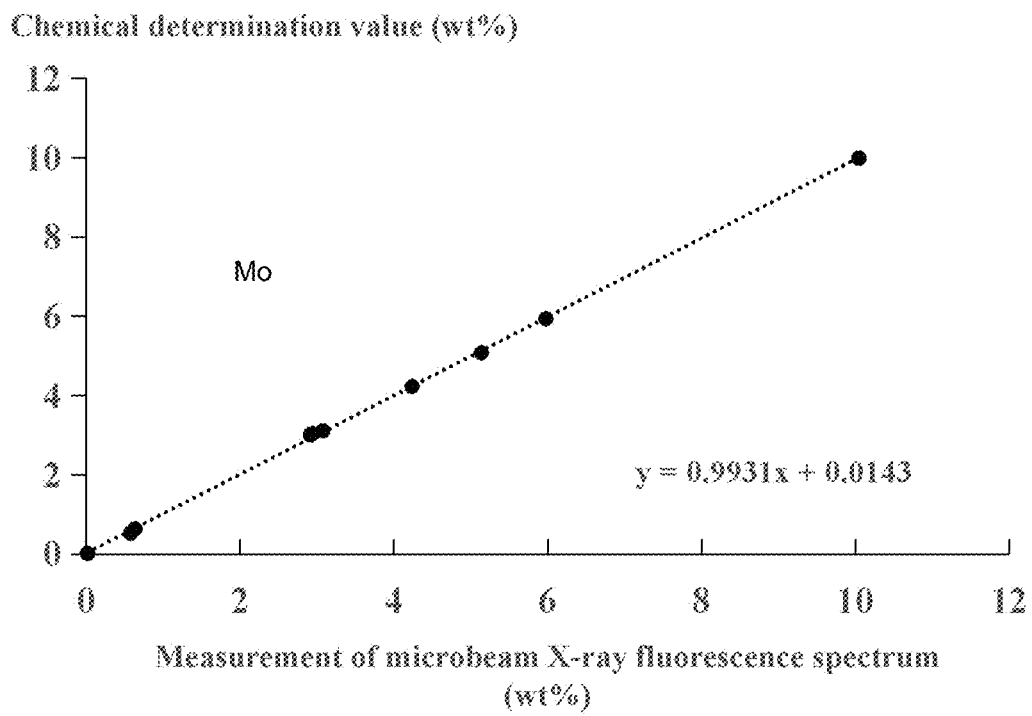
FIG. 1 is a schematic diagram showing chemical determination values of Mo element.
Figure 2:
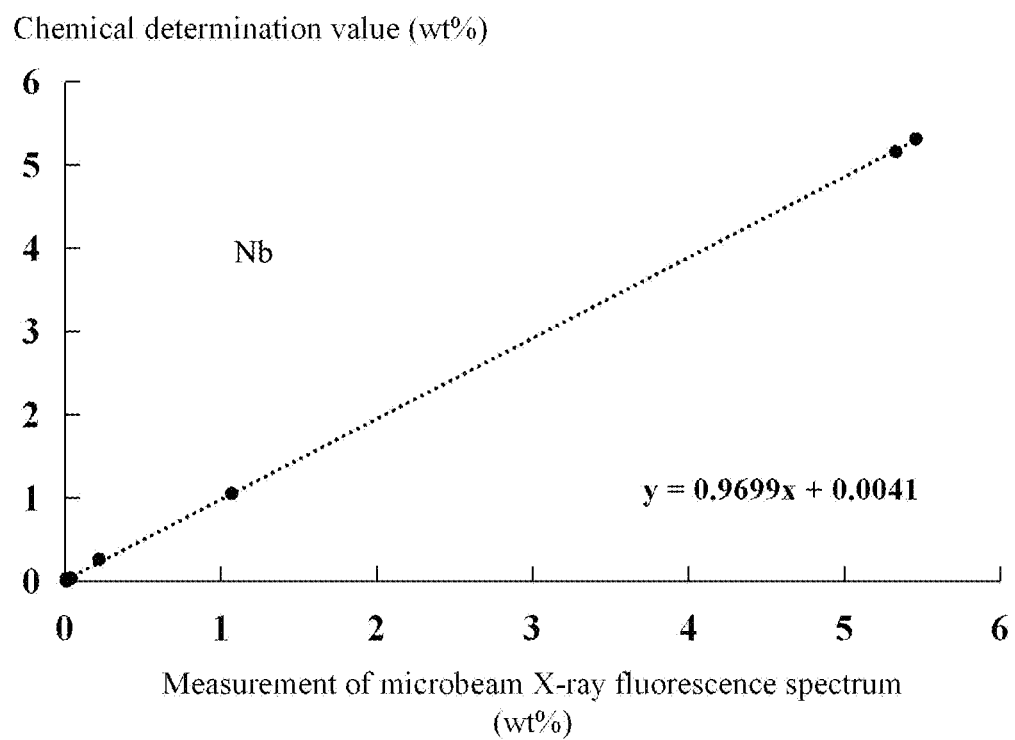
FIG. 2 is a schematic diagram showing chemical determination values of Nb element.
Figure 3:
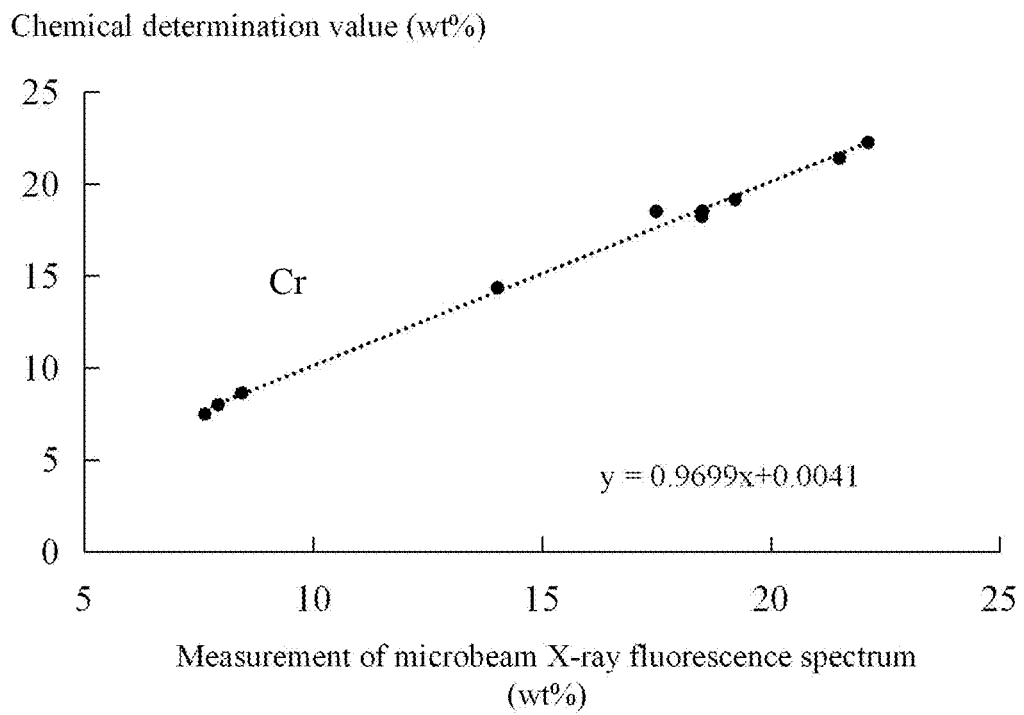
FIG. 3 is a schematic diagram showing chemical determination values of Cr element.
Figure 4:
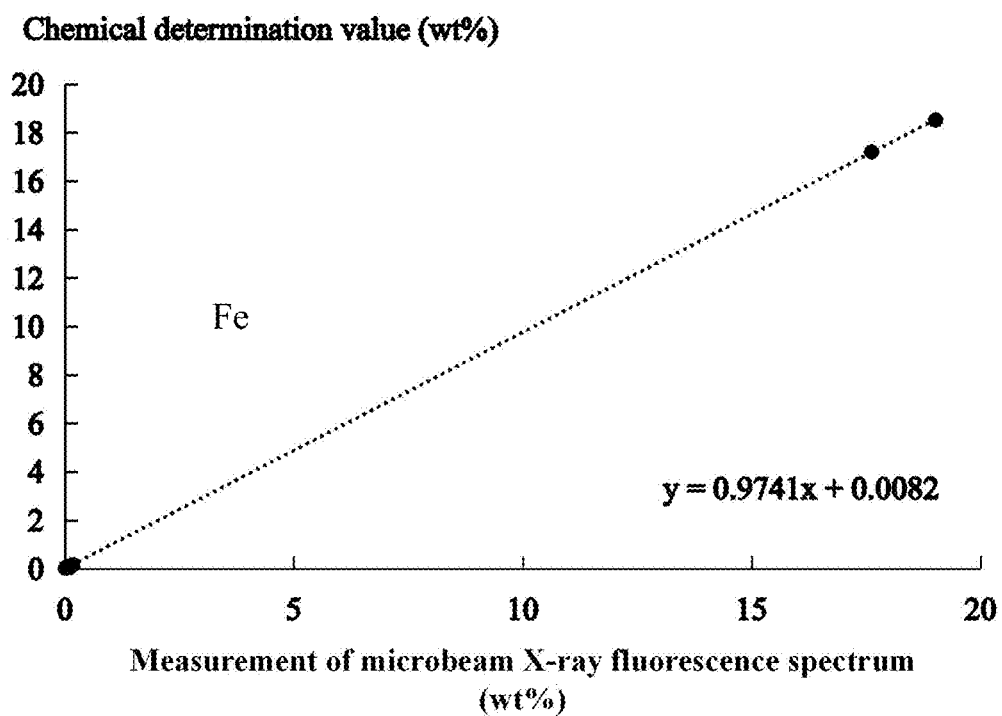
FIG. 4 is a schematic diagram showing chemical determination values of Fe element.
Figure 5:
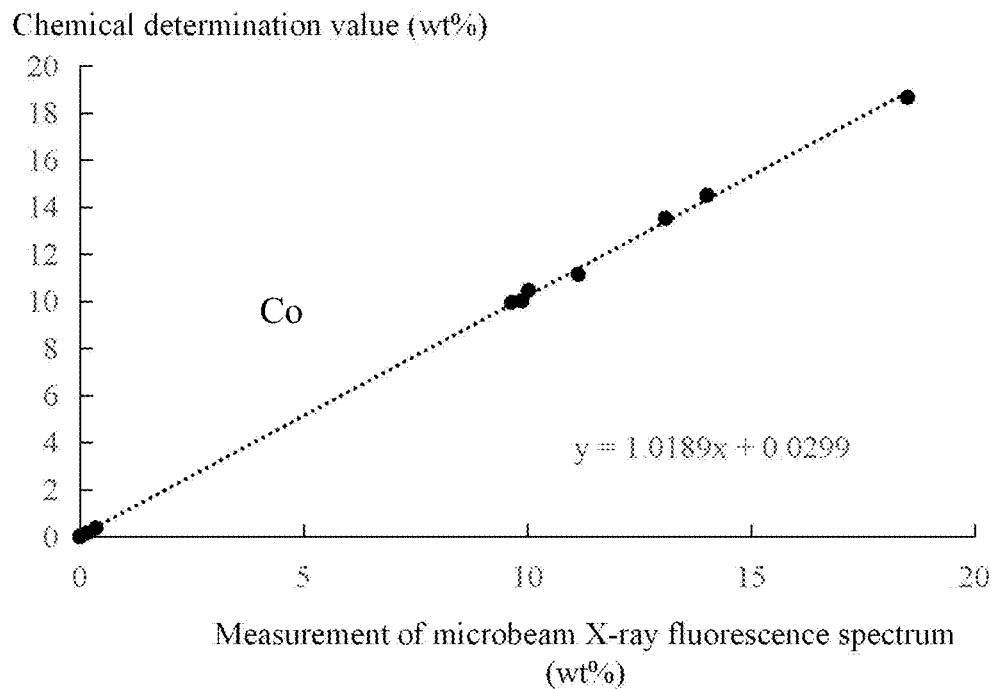
FIG. 5 is a schematic diagram showing chemical determination values of Co element.
Figure 6:
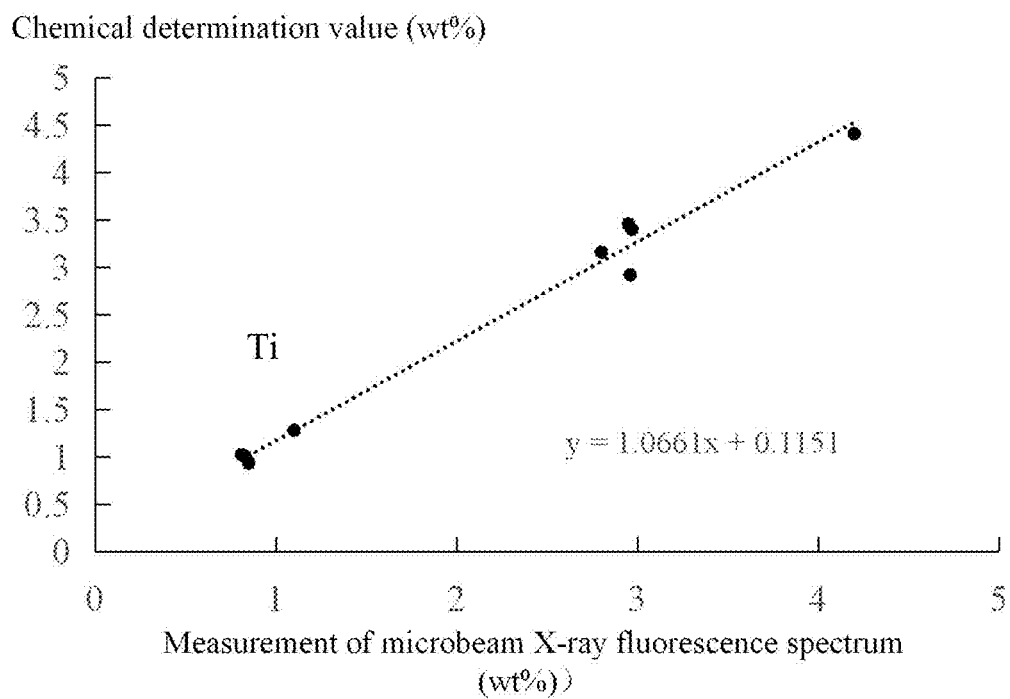
FIG. 6 is a schematic diagram showing chemical determination values of Ti element.
Figure 7:
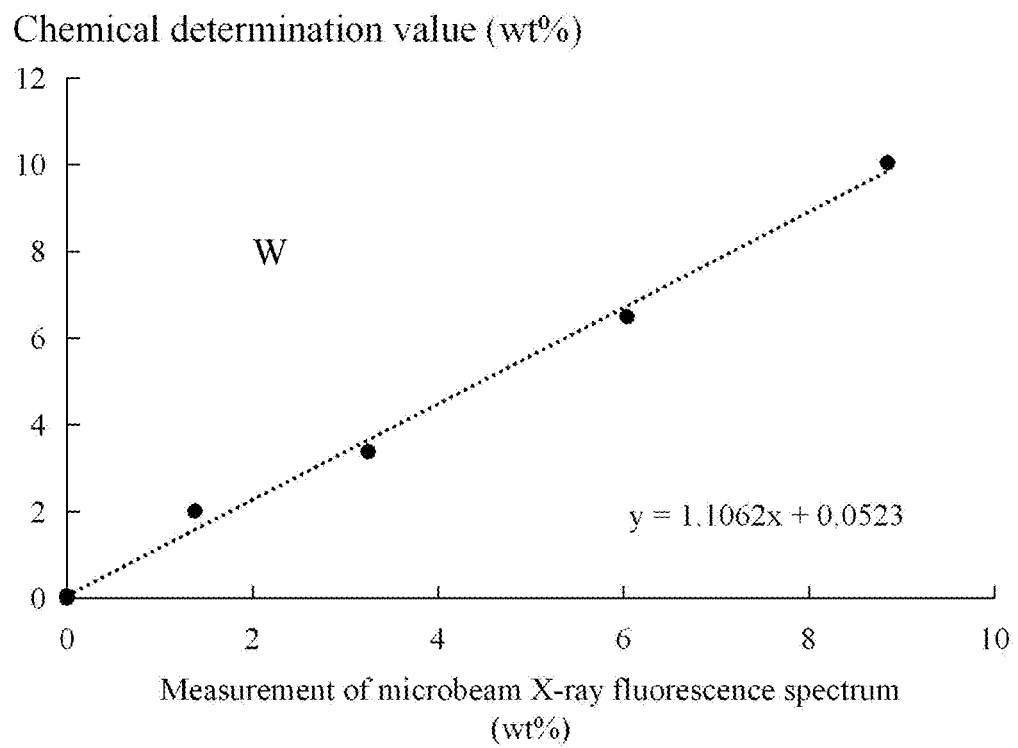
FIG. 7 is a schematic diagram showing chemical determination values of W element.
Figure 8:
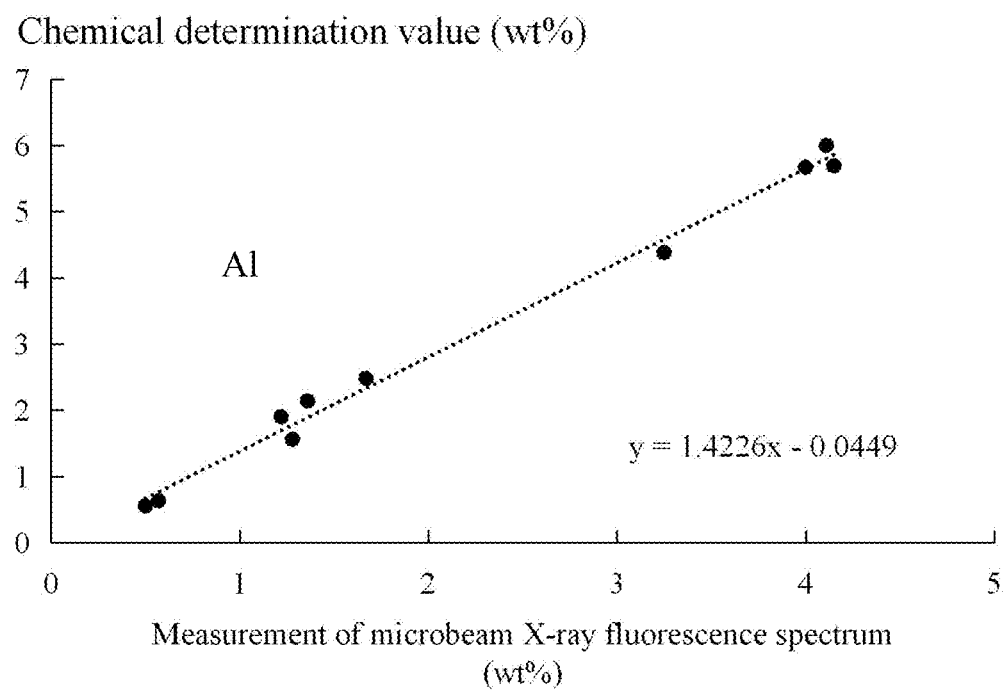
FIG. 8 is a schematic diagram showing chemical determination values of Al element.
Figure 9:
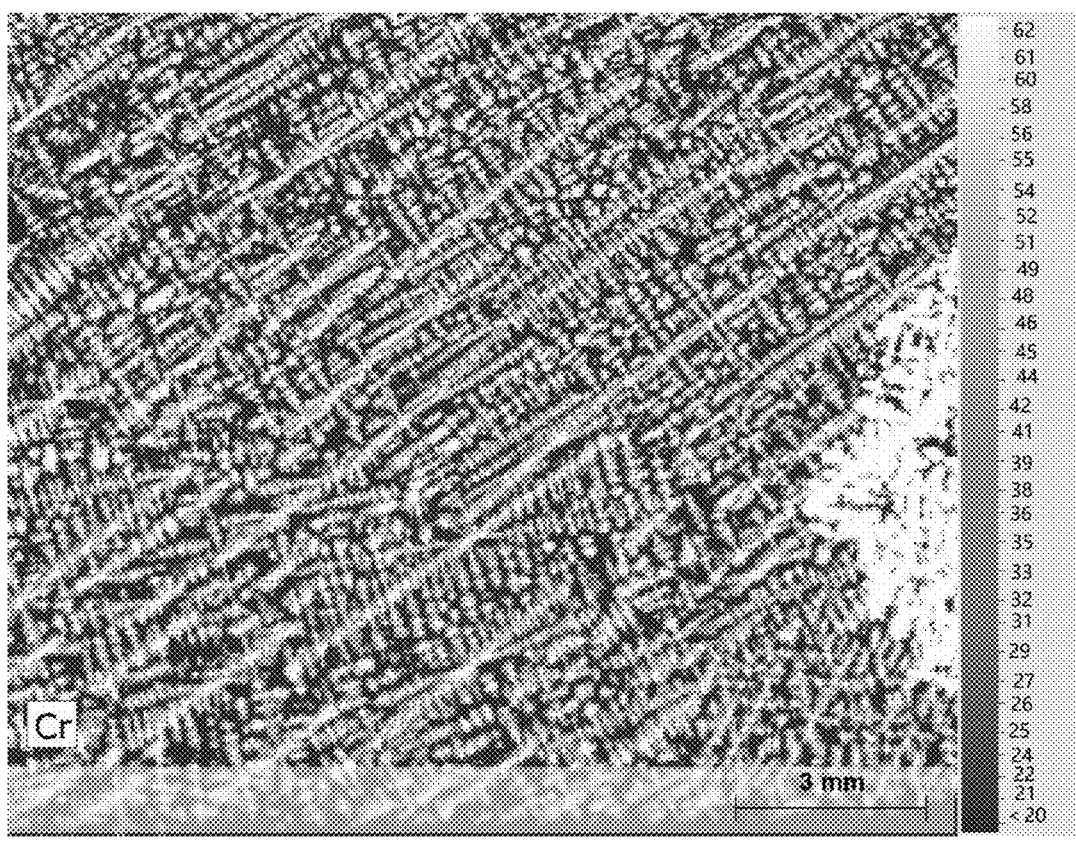
FIG. 9 is a signal intensity distribution diagram of Cr element provided by the present disclosure.
Figure 10:
FIG. 10 is a signal intensity distribution diagram of Fe element provided by the present disclosure.
Figure 11:
FIG. 11 is a signal intensity distribution diagram of Nb element provided by the present disclosure.
Figure 12:
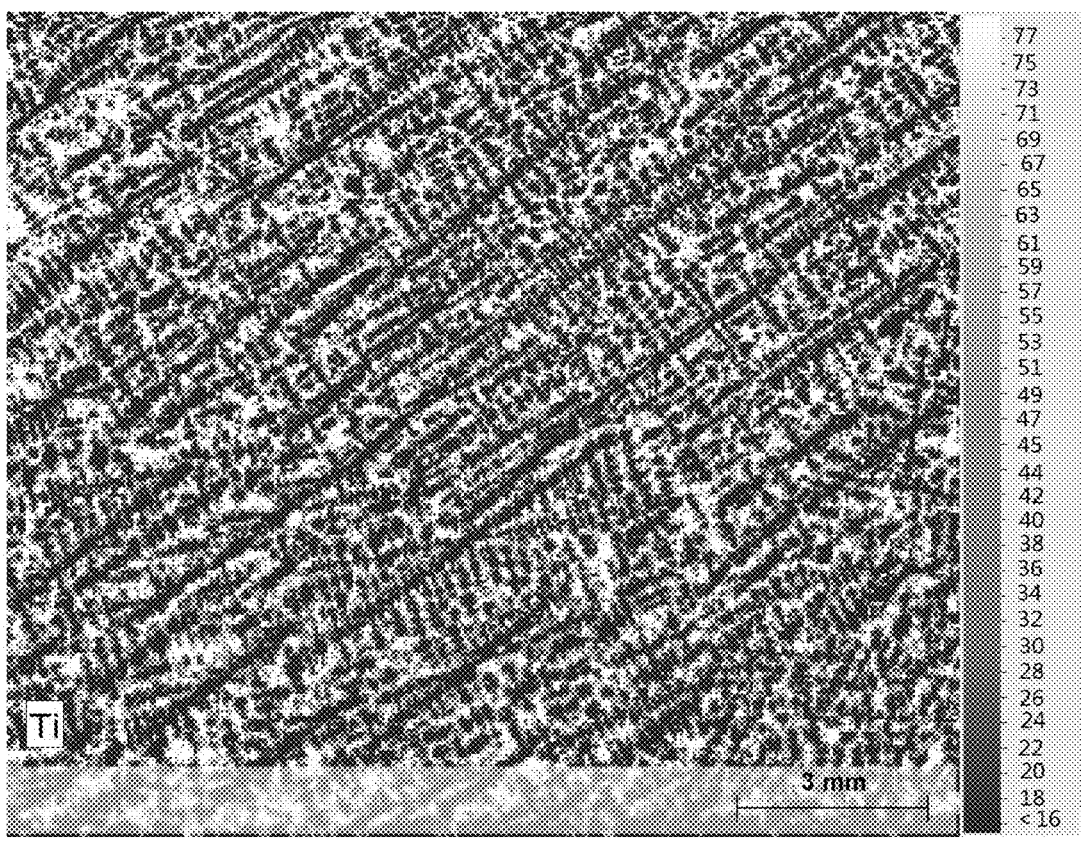
FIG. 12 is a signal intensity distribution diagram of Ti element provided by the present disclosure.
Figure 13:
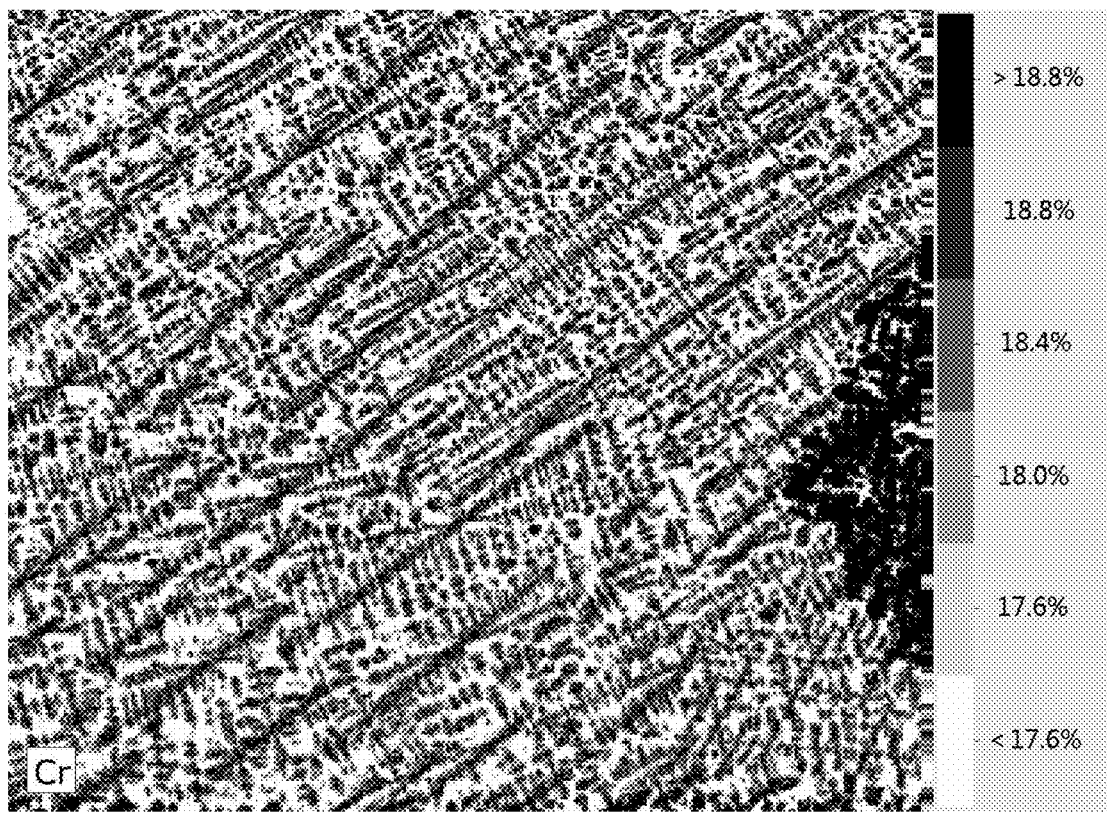
FIG. 13 is a distribution diagram of the content of Cr element and the distribution orientation of primary dendritic arms provided by the present disclosure.
Figure 14:
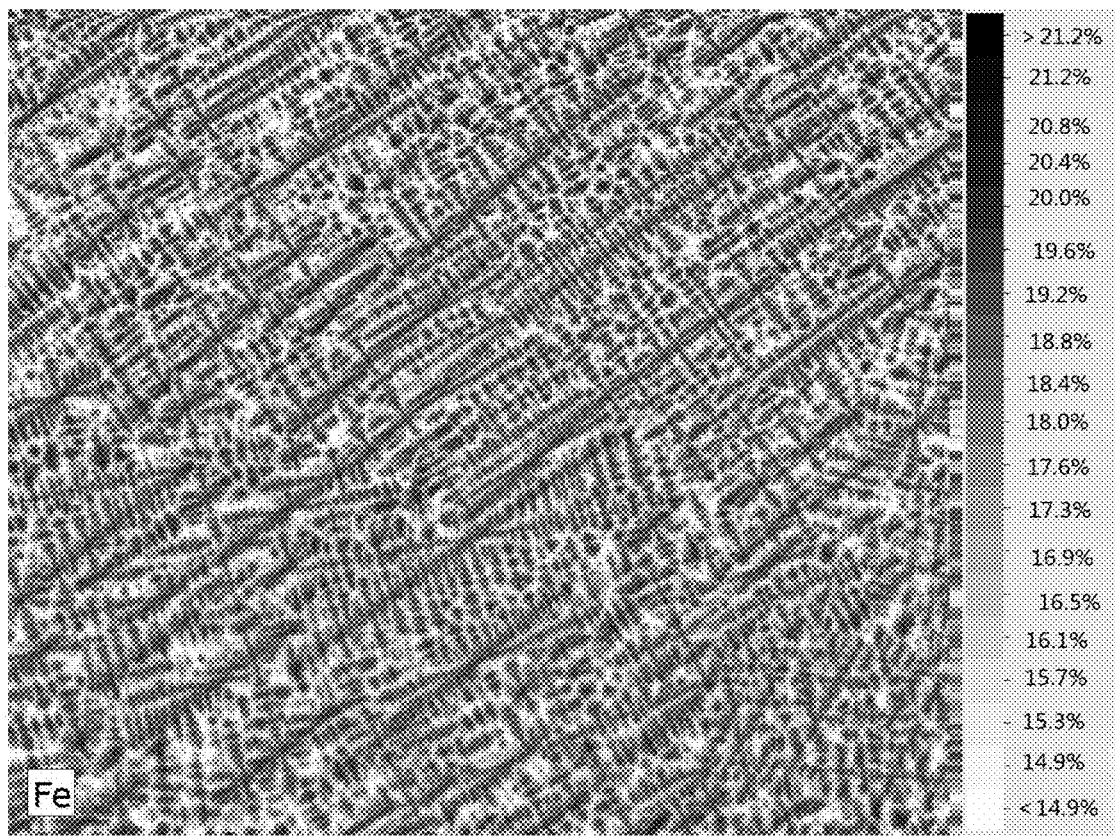
FIG. 14 is a distribution diagram of the content of Fe element and the distribution orientation of primary dendritic arms provided by the present disclosure.
Figure 15:
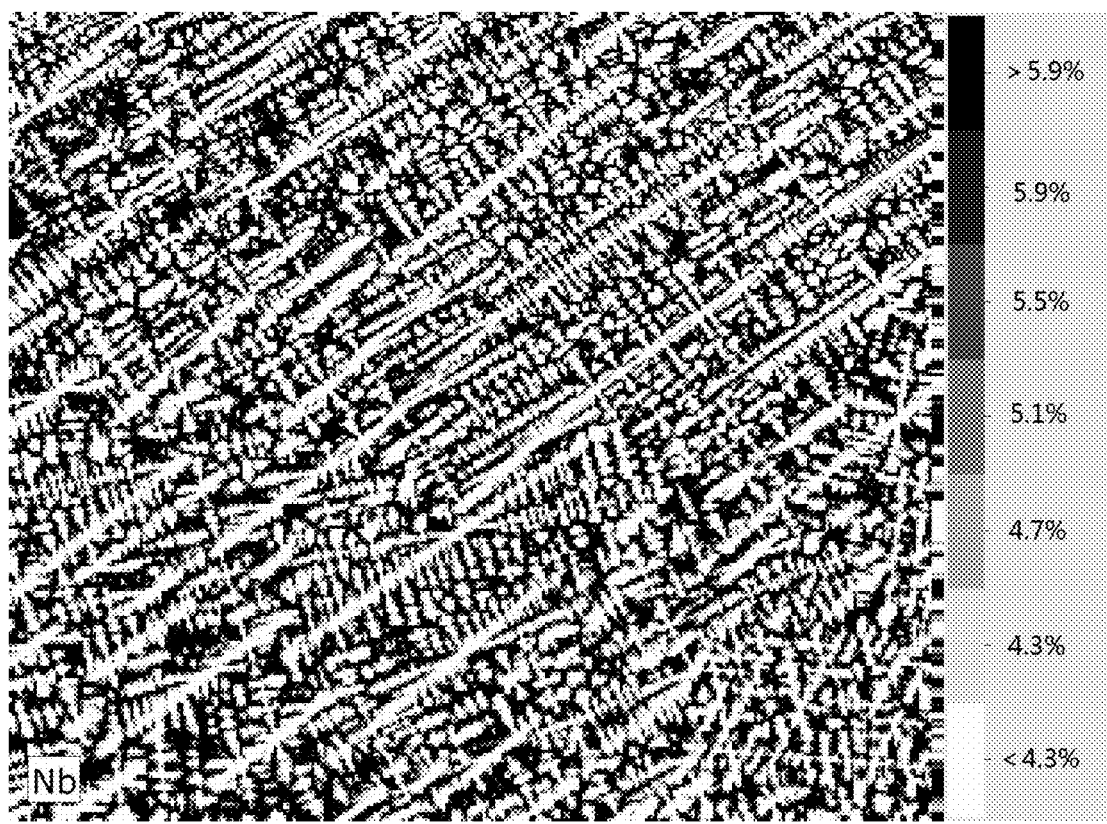
FIG. 15 is a distribution diagram of the content of Nb element and the distribution orientation of primary dendritic arms provided by the present disclosure.
Figure 16:
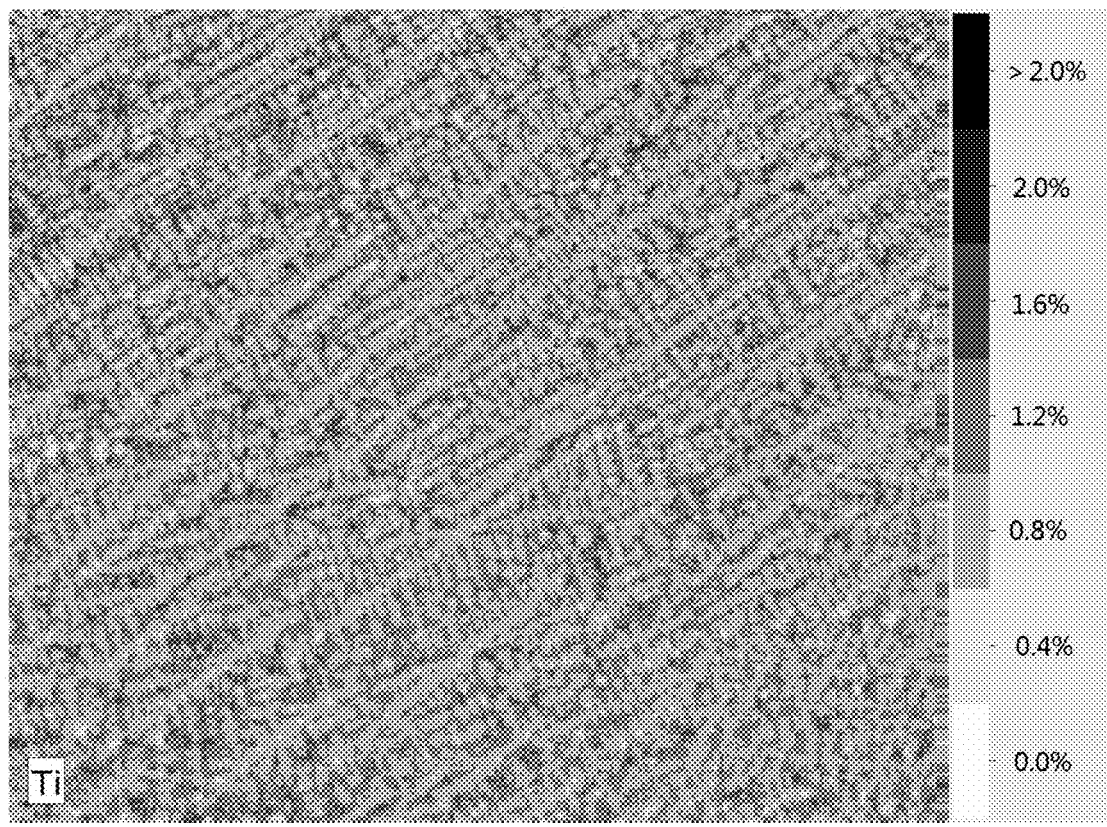
FIG. 16 is a distribution diagram of the content of Ti element and the distribution orientation of primary dendritic arms provided by the present disclosure.

In order to enable those skilled in the art to better understand the technical scheme of the present disclosure, the present disclosure will be further described in detail below with reference to the accompanying drawings.

The present disclosure provides a method for quantitatively characterizing a dendrite segregation and dendrite spacing of a high-temperature alloy ingot as shown in FIGS. 1-8, and the specific operating steps are as follows:

step 1: preparation and surface treatment of the high-temperature alloy ingot, cutting off a certain size block high-temperature alloy ingot sample, and grinding or polishing a characteristic section, wherein the size of a section to be measured of the massive polycrystalline high-temperature alloy is larger than 10 mm×10 mm, and the section to be measured is cut along a solidification heat transfer direction of liquid metal;

step 2: selection of a calibration sample and determination of an element content, selecting a series of block spectrum standard samples or uniform block alloys with a element composition and structure close to those of the high-temperature alloy sample, wherein the series of bulk spectral standard samples or uniform bulk alloy matrix are matched with the sample to be tested, all elements of the sample to be tested are contained in the series of bulk samples, and the element content of the sample to be tested is also within the range of the maximum value and minimum element content of the series of bulk samples, determining the content of each element in a calibration sample by adopting a chemical national standard method to obtain a chemical composition analysis result of the calibration sample, and grinding or polishing the surface of the calibration sample;

step 3: establishment of a quantitative method for elements in a micro-beam X-ray fluorescence spectrometer, measuring a calibration sample by using the micro-beam X-ray fluorescence spectrometry, obtaining an instrument initial element quantitative analysis result, wherein the micro-beam X-ray fluorescence spectrum is provided with a sample moving platform with the repeated positioning accuracy being less than or equal to 3 μm, an analysis beam spot of the micro-beam X-ray fluorescence spectrum is adjustable to 5 μm at least, an instrument initial element quantitative analysis result is a result obtained by a general quantitative method provided by the instrument, and a data result is affected by the composition and structure of a sample and there is a certain deviation between the data and the true content, and a linear regression fitting is performed on the chemical composition analysis result in the step 2 and the fluorescence spectrum initial determination result by a single linear fitting method, and the fitting equation is as follows:

$$C=KC_0+a$$

wherein C0 is the initial element quantitative analysis content of the instrument, C is the content after element calibration, K and a are constants, performing a linear regression fitting on that chemical component analysis result in the step 2 and the initial measurement result of the fluorescence spectrum to obtain a calibration equation of the element content of the high temperature alloy;

step 4: quantitative distribution analysis of element components of the high-temperature alloy, performing an analysis and test on the high-temperature alloy bulk sample by using the micro-beam X-ray fluorescence spectrometry under the same conditions in step 3, calibrating an element content of the obtained data matrix by using the quantitative calibration equation in step 3 to obtain a two-dimensional distribution map of the content of each element, the distribution orientation of the primary dendritic structure and the space between adjacent primary dendrites; wherein the distribution orientation of the primary dendrite structure is the directionality of the primary dendrite arm of the ingot casting, an included angle mark between the primary dendrite arm and the X direction can be used to form a line segment perpendicular to two adjacent parallel primary dendrite arms, the coordinates of the intersection points with the centers of the two adjacent primary dendrite arms are recorded, and the distance between the adjacent primary dendrites is calculated according to the two point coordinates, and the calculation formula is as follows:

$$D=\sqrt{(X_2-X_1)^2+(Y_2-Y_1)^2}$$

wherein (X1, Y1) is an intersection of a vertical line and the center of the first primary dendritic arm, (X2, Y2) is an intersection of the vertical line and the center of the second primary dendritic arm, and D is an adjacent primary dendritic spacing;

step 5: quantitative characterization of characteristic element line distribution of high-temperature alloy, according to the two-dimensional element content distribution map obtained in step 4, selecting elements with obvious dendrite distribution characteristics for line distribution quantitative characterization to obtain a characteristic element content line distribution map.

step 6: analysis of a characteristic element line distribution map and statistics of a secondary dendrite spacing, calculating an average spacing of the secondary dendrite and a segregation ratio of the element within the range according to the line distribution map of the characteristic element, wherein an element segregation ratio (SR) on the secondary dendritic gap and the dendritic arm can be calculated according to the content on the line distribution map, and the calculation formula is:

$$S_R=C_1/C_2$$

wherein C1 is the content of elements on the secondary dendrite gap, and C2 is the content of elements on the secondary dendrite arm;

and the following formula is used to calculate the secondary average spacing:

$$\lambda=(X_2-X_1)/d$$

wherein, X2 is the position when the element content of the secondary dendritic gap on the right side of the line distribution chart has a regional extreme value, X1 is the position when the element content of the secondary dendritic gap on the left side of the line distribution chart has a regional extreme value, D is the number of secondary dendritic arms contained between two locations in the profile.

EMBODIMENT

Step 1: Preparation and Surface Treatment of GH4169 High-Temperature Alloy Ingot Taking 20×20×10 mm (length×width×height) massive GH4169 high temperature alloy ingot, along the direction of solidification heat transfer cross section size is 20×20×20 mm, using a grinder to finish the section to be measured, grinding smooth surface, surface roughness Ra≤0.2 μm.

Step 2: Preparation of a Calibration Sample and Determination of an Element Content Taking a series of 30×30×20 mm (length×width×height) massive high temperature alloy samples which are close to the composition and structure of the GH4169 alloy to be tested, wherein the elements contained in the samples contain the constituent elements of the sample to be tested, and performing homogenization heat treatment on the samples to be taken as calibration samples for quantitative analysis of the metal material components, uniformly dividing the sample into two parts along the height direction, drilling a chip-shaped sample on the divided section of one sample and mixing uniformly, measuring the content of elements such as Cr, Mo, Al, Nb, Ti, Fe and the like in the chip-shaped calibration sample by an inductively coupled plasma spectrometry to obtain a chemical composition analysis result of the calibration sample, as shown in Table 1, the content of each element in GH4169 is included in the range of the element content of this series of calibration samples, and the cut section of another retained sample is ground or polished.

TABLE 1

Chemical composition analysis results (wt %) of calibration samples

| No. | Cr | Mo | Ti | Al | Co | Ta | W | Nb | Fe | Ni |
|---|---|---|---|---|---|---|---|---|---|---|
| BS718D | 18.23 | 3 | 0.93 | 0.631 | 0.368 | 0 | 0.049 | 5.16 | 18.51 | Bal. |
| IARM 277A/G | 14.35 | 4.22 | 3.4 | 4.38 | 14.5 | 0.02 | 0.047 | 0.034 | 0.16 | Bal. |
| IARM 325A/G | 18.52 | 9.98 | 3.16 | 1.56 | 10.46 | 0.003 | 0.03 | 0.007 | 0.07 | Bal. |
| IMZ180 | 7.98 | 5.93 | 1.02 | 6 | 9.95 | 4.26 | 0.05 | 0.025 | 0.073 | Bal. |
| IMZ182 | 8.63 | 3.1 | 4.69 | 5.69 | 13.52 | 0 | 0 | 0 | 0.04 | Bal. |
| IMZ202 | 8.39 | 0.63 | 1.01 | 5.67 | 10.02 | 3.25 | 10.04 | 0.028 | 0.024 | Bal. |
| IN718 | 19.14 | 3.04 | 0.938 | 0.504 | 0.145 | 0.003 | 0.021 | 5.31 | 17.2 | Bal. |
| GH708 | 18.51 | 5.07 | 1.28 | 2.14 | 0 | 0 | 6.49 | 0 | 0.05 | Bal. |
| IN939 | 22.12 | 0.008 | 3.46 | 1.9 | 18.66 | 1.4 | 2.01 | 1.05 | 0.038 | Bal. |
| K452 | 21.04 | 0.52 | 2.97 | 2.48 | 11.14 | 0 | 3.38 | 0.26 | 0.076 | Bal. |

Step 3: Establishment of a Quantitative Method for Elements in a Micro-Beam X-Ray Fluorescence Spectrometer According to the element content of GH4169, setting the instrument parameters such as light pipe voltage, current and acquisition time of the fluorescence spectrometer, and selecting the X-ray light pipe voltage of 40 KV, current of 200 μA and single pixel acquisition time of 200 ms to ensure sufficient fluorescence counting intensity of each element, taking a sample moving platform with a repetition positioning accuracy of 3 μm to match the CCD camera, the position of the platform and the sample analysis area are observed with a 100× magnifying lens, determining the cross section of the other calibration sample retained in the step two by adopting a surface analysis mode, wherein the area of the scanning area is set to be 6 mm×6 mm, performing linear fitting between the obtained initial element content measurement value of the micro-beam X-ray fluorescence spectrum and the chemical method measurement value obtained by inductively coupled plasma as the obtained instrument element quantitative analysis result, the fitting curve and fitting equation are shown in FIGS. 1-8, and the fitting equation can be used as a calibration equation for element content of high-temperature alloy.

Figure 17:
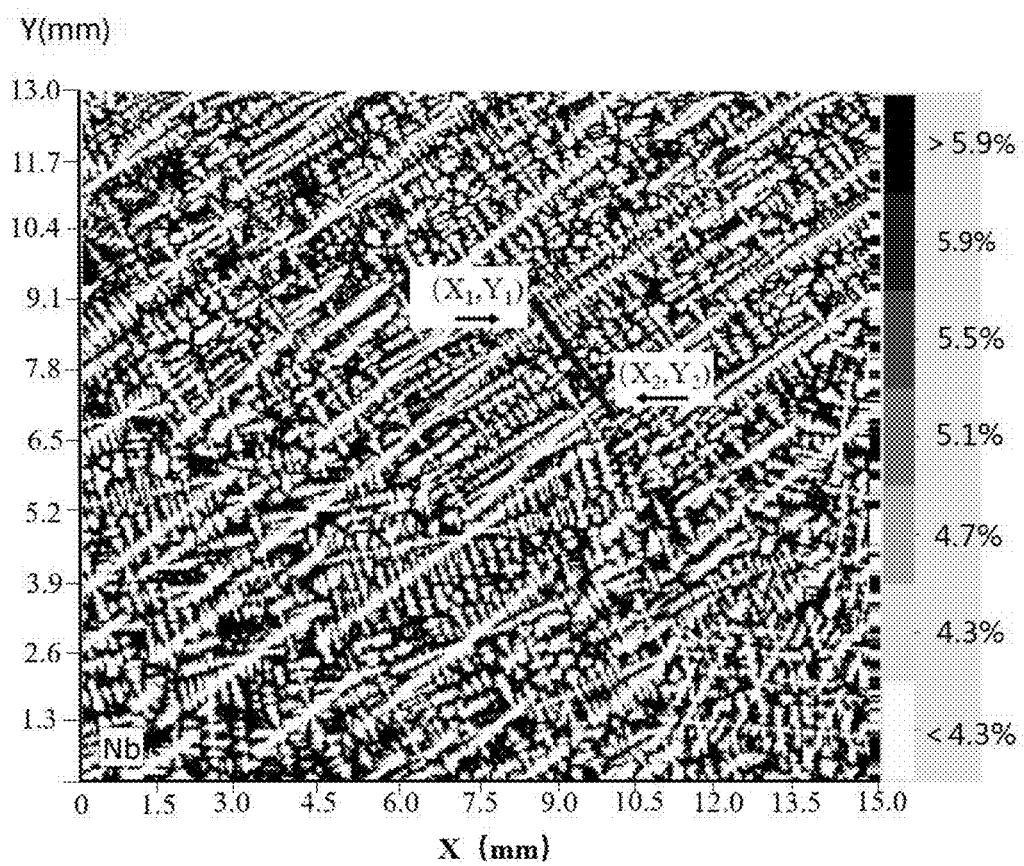
FIG. 17 is a position of a primary dendrite measurement point provided by the present disclosure.

Step 4: Quantitative Distribution Analysis of Element Components of the High-Temperature Alloy Setting the scanning area to be 15 mm×13 mm, adopting the same instrument conditions as the calibration sample surface analysis in step 3 to analyze and test the GH4169 alloy to be tested, and the signal intensity distribution chart of Fe, Cr, Nb and Ti elements (as shown in FIGS. 9-12) is obtained, and the initial values of the content distribution of Fe, Cr, Nb and Ti elements are obtained by using the instrument general quantitative software. Calibrating the obtained initial element content data matrix by using the quantitative calibration equation in step 3 to obtain a two-dimensional distribution map of the content of each element and the distribution and orientation of the primary dendritic structure (as shown in FIGS. 13-16), and it is known that all of the four elements show obvious dendritic segregation, wherein, Fe and Cr present positive segregation on the primary dendritic arm and the secondary dendritic arm, while Nb and ti present obvious negative segregation, and the angle between the primary dendritic arm and the X direction is mainly within 30-40 degrees, making a line segment perpendicular to the two adjacent and parallel primary dendritic arms and the intersection point with the centers of the two primary dendritic arms (as shown in FIG. 17), wherein the coordinate of the readable first point (X1, Y1) are (8.7, 8.6) and the coordinates of the second point (X2, Y2) are (9.8, 7.2), according to the following formula, the distance between the two primary dendrites can be calculated as 1.78 mm;

$$D=\sqrt{(X_2-X_1)^2+(Y_2-Y_1)^2}$$

Figure 18:
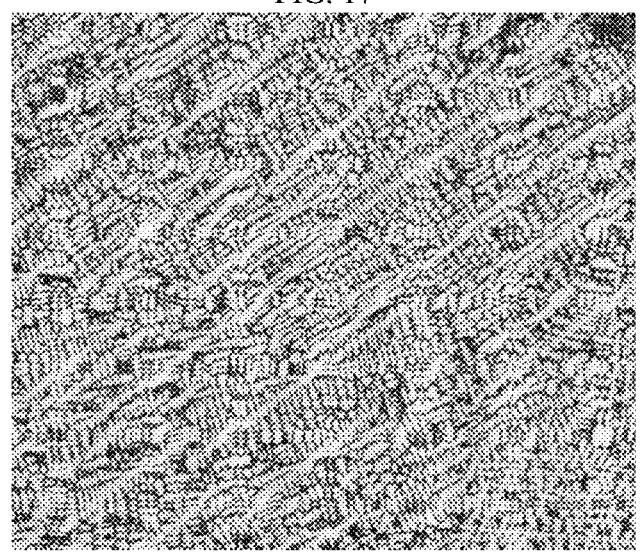
FIG. 18 is a metallographic diagram of the corroded dendritic structure provided by the present disclosure.

For comparison, after the surface to be tested is polished, a 2.5% CuCl2 (m/V)+50% hydrochloric acid (V/V)+50% ethanol (V/V) solution is used for metallographic corrosion, and the morphology of the corroded dendritic structure is shown in FIG. 18, and it can be seen that the distribution patterns of Fe, Cr, Nb and Ti elements obtained by micro-beam X-ray fluorescence spectrum are basically consistent with the metallographic patterns of dendrite structure obtained after corrosion, so the distribution of these characteristic elements can be used to identify the distribution of dendrite structure.

Figure 19:
FIG. 19 is a line scan direction and region provided by the present disclosure.

Step 5: Quantitative Characterization of Characteristic Element Line Distribution of High-Temperature Alloy According to the distribution and orientation of the primary dendritic arms in FIGS. 9-12, the angle of the cross section is adjusted so that the primary dendritic arms are parallel to the X direction and the line scanning area (as shown in FIG. 19). When calculating the secondary dendrite spacing, more than three secondary dendrite arms must be included in the starting and ending ranges of line distribution, the pixel spacing≤5 μm, the single pixel acquisition time the fluorescence signal of each element>10000 cps, and the acquisition time of each pixel is set to 10 s when determining the line distribution. The obtained content line distribution diagram of Nb element is shown in FIG. 20.

Figure 20:
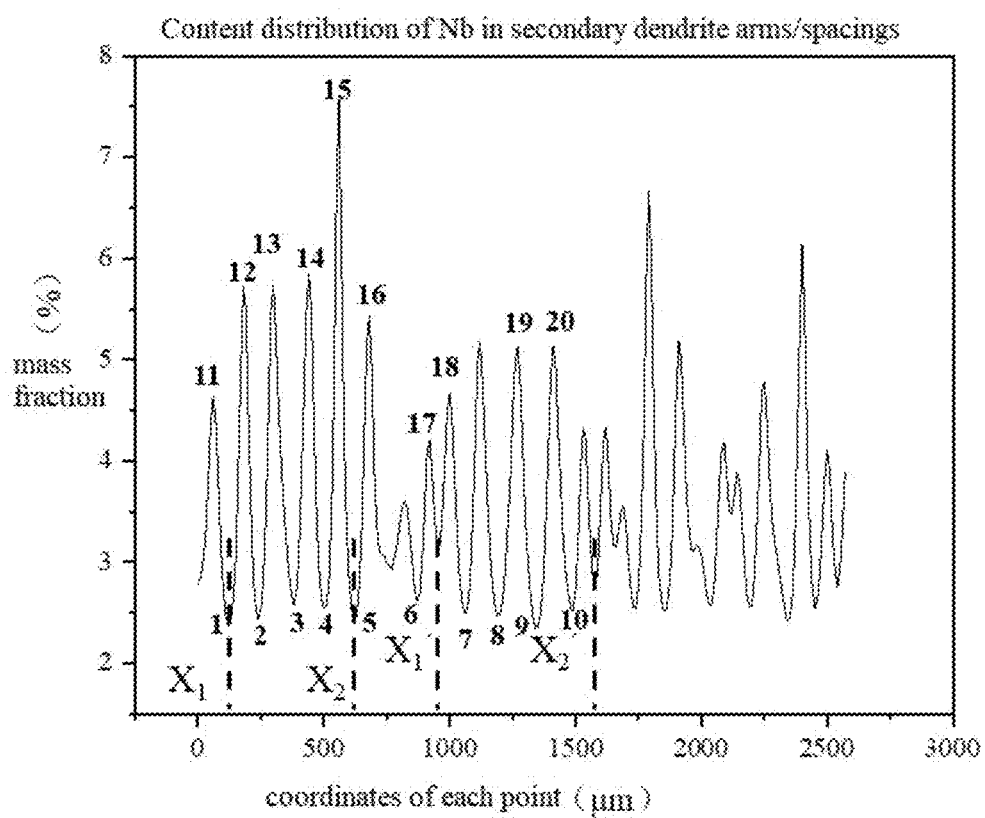
FIG. 20 is a distribution diagram of the content line of Nb element and the positions of each sampling point provided by the present disclosure.
Figure 21:
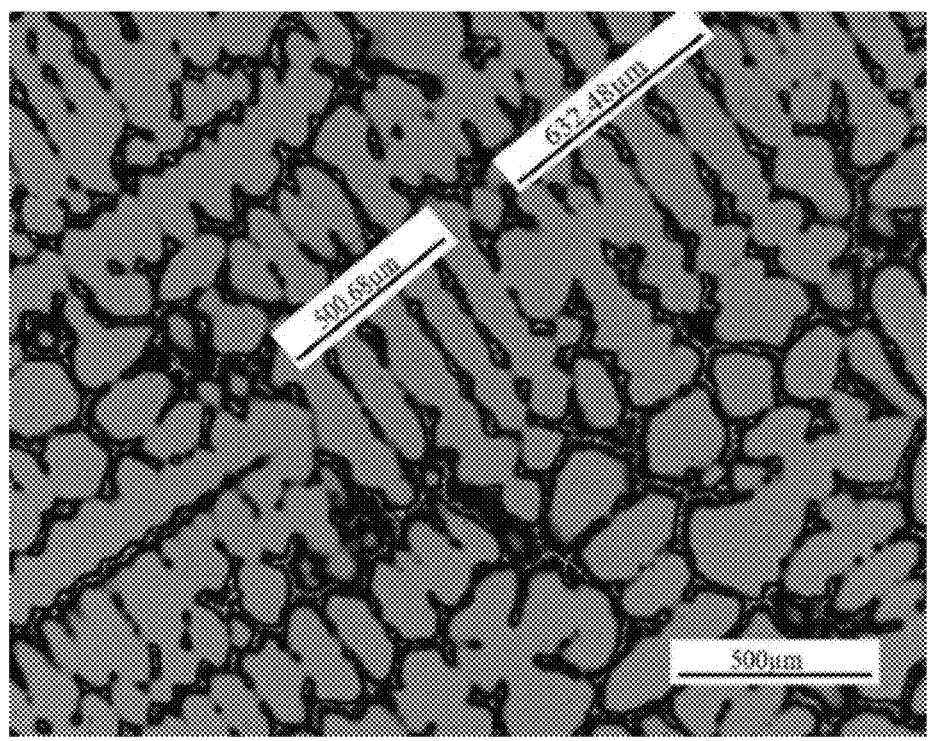
FIG. 21 is a measurement area of secondary dendrite spacing of a dendritic structure after metallographic corrosion provided by the present disclosure.

Step 6: Analysis of a Characteristic Element Line Distribution Map and Statistics of a Secondary Dendrite Spacing Calculating the average spacing of the secondary dendrites of two adjacent areas according to the line distribution diagram of Nb element, wherein the two adjacent areas are shown by marks in the line distribution diagram FIG. 20, one area contains four complete secondary dendrite arms, the X coordinate of the left starting point is 130μ m(X1), the X coordinate of the right ending point is 630 μm(X2), according to the formula, the average quadratic spacing is 125 μm, the second region contains five complete secondary dendrite arms, the left starting point X coordinate is 970 μm (X1'), and the right ending point X coordinate is 1590 μm (X2'), and using the formula λ=(X_2-X_1)/d to calculate, the average quadratic spacing is 124 μm;

reading the element content between the secondary dendrites at points 1-10 in FIG. 20 from the content line distribution data, the average value of ten points is obtained, and the results are shown in Table 2, and reading the element content on the dendritic arm at points 11-20 in FIG. 18 from the content line distribution data, the average value of ten points is obtained, and the results are shown in Table 5, the element segregation ratio (SR) between dendrites and on dendrites of secondary dendrites can be calculated according to the content of linear distribution diagram, and the formula is:

$$S_R = C_1/C_2$$

wherein, C1 is the average element content between dendrites, C2 is the average element content of dendrite dry, dividing the average element content between dendrites by the average element content on the secondary dendritic arm to obtain the element segregation ratio on the secondary dendritic arm, The results are shown in Table 4.

TABLE 2

Element Content on Secondary Dendrite at Point 1-10 (wt %)

| No. | Al | Ti | Cr | Fe | Co | Ni | Nb | Mo |
|---|---|---|---|---|---|---|---|---|
| 1 | 0.46 | 1.07 | 18.26 | 17.75 | 0.01 | 54.90 | 4.63 | 2.92 |
| 2 | 0.38 | 1.20 | 18.01 | 17.38 | 0.00 | 54.31 | 5.72 | 2.99 |
| 3 | 0.41 | 1.16 | 17.80 | 17.14 | 0.00 | 54.75 | 5.72 | 3.02 |
| 4 | 0.53 | 1.18 | 17.64 | 16.99 | 0.01 | 54.79 | 5.85 | 3.01 |
| 5 | 0.46 | 1.22 | 17.39 | 16.58 | 0.00 | 53.65 | 7.58 | 3.11 |
| 6 | 0.42 | 1.07 | 18.11 | 17.57 | 0.00 | 54.40 | 5.44 | 2.99 |
| 7 | 0.49 | 0.99 | 18.66 | 18.20 | 0.01 | 54.61 | 4.21 | 2.82 |
| 8 | 0.31 | 1.05 | 18.37 | 17.77 | 0.00 | 54.88 | 4.67 | 2.95 |
| 9 | 0.36 | 1.09 | 18.07 | 17.41 | 0.01 | 54.87 | 5.18 | 3.01 |
| 10 | 0.44 | 1.15 | 18.04 | 17.32 | 0.01 | 54.95 | 5.12 | 2.98 |
| average value | 0.43 | 1.12 | 18.03 | 17.41 | 0.00 | 54.61 | 5.41 | 2.98 |

TABLE 3

Element Content on Dendritic Arm at Point 11-20 (wt %)

| No | Al | Ti | Cr | Fe | Co | Ni | Nb | Mo |
|---|---|---|---|---|---|---|---|---|
| 11 | 0.61 | 0.72 | 19.36 | 19.72 | 0.01 | 54.68 | 2.37 | 2.53 |
| 12 | 0.43 | 0.73 | 19.33 | 19.72 | 0.01 | 54.79 | 2.43 | 2.56 |
| 13 | 0.43 | 0.79 | 19.22 | 19.40 | 0.01 | 54.84 | 2.70 | 2.61 |
| 14 | 0.48 | 0.75 | 19.30 | 19.64 | 0.00 | 54.74 | 2.55 | 2.54 |
| 15 | 0.43 | 0.71 | 19.35 | 19.73 | 0.02 | 54.80 | 2.40 | 2.56 |
| 16 | 0.60 | 0.78 | 19.29 | 19.44 | 0.01 | 54.69 | 2.62 | 2.57 |
| 17 | 0.44 | 0.73 | 19.30 | 19.63 | 0.01 | 54.87 | 2.49 | 2.54 |
| 18 | 0.40 | 0.72 | 19.30 | 19.59 | 0.01 | 54.96 | 2.47 | 2.54 |
| 19 | 0.49 | 0.71 | 19.38 | 19.72 | 0.01 | 54.80 | 2.34 | 2.56 |
| 20 | 0.51 | 0.75 | 19.30 | 19.57 | 0.02 | 54.76 | 2.52 | 2.57 |
| average value | 0.48 | 0.74 | 19.31 | 19.62 | 0.01 | 54.79 | 2.49 | 2.56 |

TABLE 4

Segregation Ratio of Each Element

| number | Al | Ti | Cr | Fe | Co | Ni | Nb | Mo |
|---|---|---|---|---|---|---|---|---|
| $S_R$ | 0.88 | 1.51 | 0.93 | 0.89 | 0.41 | 1.00 | 2.18 | 1.17 |

In order to compare that reliability of the method, the dendrite structure in the present area is revealed by adopting the metallographic etching method, and the dendrite structure image is collected by adopting the metallographic microscope, and the distance between the centers of multiple secondary dendrite arms is measured in conjunction with quantitative metallography software (as shown in FIG. 19), and it can be seen that the line segment 1 includes four secondary dendritic pitches with a total length of 500.68 μm and an average secondary dendritic pitch of 125.2 μm, the line segment 2 includes five secondary dendritic pitches with a total length of 632.48 μm, and the average secondary dendrite spacing is 126.5 μm, which is in good agreement with this method.

Some exemplary embodiments of the present disclosure have been described above by way of illustration only, and it is needless to say that those skilled in the art can modify the described embodiments in various ways without departing from the spirit and scope of the present disclosure. Therefore, the above drawings and descriptions are illustrative in nature, and should not be understood as limiting the scope of protection of the claims of the present disclosure. Any modifications, equivalent substitutions, improvements, etc. that are within the spirit and principles of the present disclosure should be included within the scope of protection of the present disclosure.

What is claimed is:

1. A method for quantitatively characterizing a dendrite segregation and dendrite spacing of a high-temperature alloy ingot, comprising:
   step 1: preparation and surface treatment of the high-temperature alloy ingot,
   cutting off a certain size block high-temperature alloy ingot sample, and grinding or polishing a characteristic section;
   step 2: selection of a calibration sample and determination of an element content,
   selecting a series of block spectrum standard samples or uniform block alloys with a element composition and structure close to those of the high-temperature alloy sample,
   measuring a content of each element in the calibration sample by using a national standard method to obtain a chemical composition analysis result of the calibration sample, and
   grinding or polishing a surface of the calibration sample;
   step 3: establishment of a quantitative method for elements in a micro-beam X-ray fluorescence spectrometer,
   measuring a calibration sample by using the micro-beam X-ray fluorescence spectrometry, obtaining an instrument initial element quantitative analysis result, and
   performing a linear regression fitting on a chemical component analysis result of step 2 and a fluorescence spectrum initial measurement result to obtain a high-temperature alloy element content calibration equation;
   step 4: quantitative distribution analysis of element components of the high-temperature alloy,
   performing an analysis and test on the high-temperature alloy bulk sample by using the micro-beam X-ray fluorescence spectrometry under the same conditions in step 3,
   calibrating an element content of the obtained data matrix by using the quantitative calibration equation in step 3 to obtain a two-dimensional distribution map of the content of each element, the distribution orientation of the primary dendritic structure and the space between adjacent primary dendrites;
   step 5: quantitative characterization of characteristic element line distribution of high-temperature alloy,
   according to the two-dimensional element content distribution map obtained in step 4, selecting elements with obvious dendrite distribution characteristics for line distribution quantitative characterization to obtain a characteristic element content line distribution map;
   step 6: analysis of a characteristic element line distribution map and statistics of a secondary dendrite spacing, calculating an average spacing of the secondary dendrite and a segregation ratio of the element within the range according to the line distribution map of the characteristic element.

2. The method of claim 1, wherein in step 1, the size of a section to be measured of the massive polycrystalline high-temperature alloy is larger than 10 mm×10 mm, and the section to be measured is cut along a solidification heat transfer direction of a liquid metal.

3. The method of claim 1, wherein in step 2, the series of bulk spectral standard samples or uniform bulk alloy matrix are matched with the sample to be tested, all elements of the sample to be tested are contained in the series of bulk samples, and the element content of the sample to be tested is also within a range of the maximum value and minimum element content of the series of bulk samples.

4. The method of claim 1, wherein in step 3, the micro-beam x-ray fluorescence spectrum is provided with a sample moving platform with the repeated positioning accuracy being less than or equal to 3 µm, an analysis beam spot of the micro-beam x-ray fluorescence spectrum is adjustable to 5 µm at least, an instrument initial element quantitative analysis result is a result obtained by a general quantitative method provided by the instrument, and a data result is affected by the composition and structure of a sample and there is a certain deviation between the data and the true content, and a linear regression fitting is performed on the chemical composition analysis result in the step 2 and the fluorescence spectrum initial determination result by a single linear fitting method, and the fitting equation is as follows:

$$C=KC_0+a$$

wherein $C_0$ is an initial element quantitative analysis content of the instrument, C is a content after element calibration, K and a are constants.

5. The method of claim 1, wherein in step 4, a distribution orientation of the primary dendrite structure is the directionality of the primary dendrite arm of the ingot, an included angle mark between the primary dendrite arm and the X direction can be used to form a line segment perpendicular to two adjacent parallel primary dendrite arms, the coordinates of the intersection points with the centers of the two adjacent primary dendrite arms are recorded, and the spacing between the adjacent primary dendrites is calculated according to the two point coordinates, and the calculation formula is as follows:

$$D=\sqrt{(X_2-X_1)^2+(Y_2-Y_1)^2}$$

wherein $(X_1, Y_1)$ is an intersection of a vertical line and the center of the first primary dendritic arm, $(X_2, Y_2)$ is an intersection of the vertical line and the center of the second primary dendritic arm, and D is an adjacent primary dendritic spacing.

6. The method of claim 1, wherein in step 5, the high-temperature alloy test rod has elements with obvious characteristic distribution on a dendritic structure, comprising elements of Nb, Fe, Cr and Ni, and the content of the elements is more than 1%.

7. The method of claim 1, wherein in step 5, the angle of a line scanning direction is adjusted according to the element intensity or content surface distribution map obtained in step 4, so that a primary dendritic arm is parallel to the x direction, and the line scanning direction is along the X direction when the secondary dendritic spacing is measured, more than three secondary dendritic arms must be included, the pixel spacing is less than or equal to 5 µm, and a single pixel acquisition time needs to ensure that an element fluorescence signal is more than 10000 cps to ensure the spatial resolution and quantitative reliability of the line distribution.

8. The method of claim 1, wherein in the step 6, the following formula is used to calculate the secondary average spacing:

$$\lambda=(X_2-X_1)/d$$

wherein, $X_2$ is a position when an element content of the secondary dendritic gap on the right side of the line distribution chart has a regional extreme value, $X_1$ is a position when an element content of the secondary dendritic gap on the left side of the line distribution chart has a regional extreme value, D is the number of secondary dendritic arms contained between two locations in the profile.

9. The method of claim 1, wherein an element segregation ratio (SR) on the secondary dendritic gap and the dendritic arm can be calculated according to the content on the line distribution map, and the calculation formula is:

$$S_R=C_1/C_2$$

wherein $C_1$ is a content of elements on the secondary dendrite gap, and $C_2$ is a content of elements on the secondary dendrite arm.

* * * * *